United States Patent
Mayer

(10) Patent No.: US 6,945,436 B2
(45) Date of Patent: Sep. 20, 2005

(54) DISPENSER FOR LIMITING MATERIAL EXTRUDED AFTER ACTUATION

(75) Inventor: Stanley Mayer, Middletown, NY (US)

(73) Assignee: Coltene/Whaledent Inc., Cuyahoga Falls, OH (US)

( * ) Notice: Subject to any disclaimer, the term of this patent is extended or adjusted under 35 U.S.C. 154(b) by 0 days.

(21) Appl. No.: 10/677,143

(22) Filed: Oct. 1, 2003

(65) Prior Publication Data

US 2004/0124215 A1 Jul. 1, 2004

Related U.S. Application Data

(60) Provisional application No. 60/415,020, filed on Oct. 1, 2002.

(51) Int. Cl.⁷ ................................................. B67D 5/42
(52) U.S. Cl. ......................................................... 222/391
(58) Field of Search ............................................. 222/391

(56) References Cited

U.S. PATENT DOCUMENTS

| | | | |
|---|---|---|---|
| 4,090,639 A | * | 5/1978 | Campbell et al. ............ 222/391 |
| 4,330,070 A | | 5/1982 | Doubleday |
| 4,655,372 A | | 4/1987 | Ross et al. |
| 4,681,524 A | | 7/1987 | Ikeda et al. |
| 5,181,636 A | | 1/1993 | Anderson et al. |
| 5,192,008 A | | 3/1993 | Hwan |
| 5,370,282 A | * | 12/1994 | Sedlmeier ................... 222/391 |
| 5,482,189 A | | 1/1996 | Dentler et al. |
| 5,529,225 A | | 6/1996 | Chang |
| 5,653,363 A | | 8/1997 | Chang |
| 6,082,597 A | | 7/2000 | Beckett et al. |
| 6,170,714 B1 | * | 1/2001 | Lesage ........................ 222/391 |
| 6,319,262 B1 | * | 11/2001 | Bates et al. ................. 606/127 |
| 6,412,667 B1 | * | 7/2002 | Huang .......................... 222/391 |

* cited by examiner

Primary Examiner—Philippe Derakshani
(74) Attorney, Agent, or Firm—Katten Muchin Rosenman LLP

(57) ABSTRACT

A dispenser for dispensing extrudable material from a cartridge. The dispenser includes a housing having a first recess for holding the cartridge, a plunger movable along the longitudinal axis of the first recess, a driver element for selectively engaging and moving the plunger in a forward direction along the longitudinal axis, and a clutch element for and selectively engaging the plunger to restrain movement of the plunger in a rearward direction. When the clutch element restrains the plunger, movement of the plunger in the rearward direction is limited to a predetermined distance.

17 Claims, 2 Drawing Sheets

US 6,945,436 B2

DISPENSER FOR LIMITING MATERIAL EXTRUDED AFTER ACTUATION

CROSS-REFERENCE TO RELATED APPLICATION

The present application claims priority under 35 U.S.C. § 119(e) from U.S. Ser. No. 60/415,020, filed on Oct. 1, 2002. U.S. Ser. No. 60/415,020 was filed by inventors common to the present application, and is hereby incorporated by reference.

FIELD OF THE INVENTION

The present invention relates to a hand-held dispenser for extruding composite dental materials, and in a particular to a hand held dispenser for avoiding continued extrusion of material following actuation of the dispenser.

BACKGROUND OF THE INVENTION

A variety of materials are commonly used in the field of dental treatment, including impression materials, filling materials, and adhering materials. Often, these materials are formed at or near the time of use from a combination of two or more kinds of component materials. For example, dentists or dental technicians may remove required amounts of the component materials from their respective containers (for example, by weight, volume or length) and place these on a mixing pad to be mixed with each other and put into use. These mixed materials may then be placed in a cartridge suitable for application using a dispenser. In other cases, non-composite and pre-mixed dental materials may be directly provided by manufacturers in dispenser cartridges.

Conventional dispensers may use a variety of means for extruding these mixed materials from a cartridge. For example, a pistol-shaped cartridge dispenser maybe used that positions the cartridge in a predetermined position at the front of the device, and employs a piston coupled to a push rod for pressing against the mixed material from an opening in the rear of the tube in order to extrude the mixed material from a nozzle positioned at the front of the tube. The piston and push rod typically move in response to a mechanical force directly applied to the dispenser by a human operator, and may alternatively move in response to a force applied by other means (for example, supplied by a pressurized fluid or electric motor).

When operating such dispensers, it is desirable to precisely control the amount of material that is extruded. If an excess of material is supplied (over-extruded), for example, the dentist or dental technician will be required to remove the over-extruded material. This creates additional work for the dentist or dental technician, and may be difficult, for example, if the extruded material is a composition that hardens quickly once extruded. Removing over-extruded material may also create discomfort and or unwanted delay for the dental patient. In particular, it is desirable to avoid continued extrusion of material from the dispenser after actuation ceases ("drooling").

SUMMARY OF THE INVENTION

The deficiencies of the prior art may be largely overcome by a novel dental composite dispenser having a mechanism for reducing drooling. In a preferred embodiment, the dispenser comprises a handle having a frontward cavity for positioning a cartridge, a piston for extruding material from the tube and a push rod for driving the piston. A driver element positioned in the housing comprises a block bored with a hole through which the push rod is inserted, the hole having a size slightly larger than that of an outer diameter of the push rod. The block, for example, may comprise a stamped metal leaf, or a stack of such leaves.

An actuator in the handle is brought into contact with a lower portion of the driver element, causing the driver element to incline and the push rod to come into contact with an edge of the hole. The actuator then causes the driver element to advance, such that a contact resistance (friction) resulting from an edge of the hole contacting the push rod advances the push rod with the driver element. Once the trigger is released, a driver spring returns the driver element to a non-inclined position so that the push rod is able to move freely through the hole in the driver element.

A clutch element positioned in the housing comprises a plate bored with a hole through which the push rod is inserted, the hole having a size slightly larger than that of the outer diameter of the push rod. The clutch element is pivotally fixed in a recess in the housing above the push rod, and remains in a non-inclined position as the push rod is advanced. Once the actuator is released, compressive energy retained in the cartridge causes push rod and the driver element to move rearward. The clutch element, urged by a clutch spring, inclines to cause the push rod to engage an edge of the hole in the clutch element. Contact resistance between the clutch element and the push rod limits rearward travel of the push rod to a distance controlled by the geometry of a cavity in the housing for confining movement of the clutch element.

The clutch element is located forward of the actuator and driving mechanism to facilitate compactness of the dispenser, and has a portion extending through a hood of the dispenser which can be pushed by finger pressure in order to return the clutch element to its non-inclined position, and thereby remove contact resistance between the clutch element and push rod so that the push rod may be retracted to its most rearward position in order, for example, to remove a spent cartridge from the dispenser and install a new cartridge.

BRIEF DESCRIPTION OF THE DRAWING

A more complete understanding of the invention may be obtained by reading the following description of specific illustrative embodiments of the invention in conjunction with the appended drawing in which.

DETAILED DESCRIPTION OF THE PREFERRED EMBODIMENTS

The following detailed description includes a description of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention.

Figure 1C:
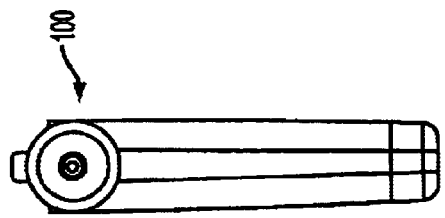
FIGS. 1A–1D respectively show front, side sectional, rear and top isometric views of a first embodiment of the present invention.
Figure 1B:
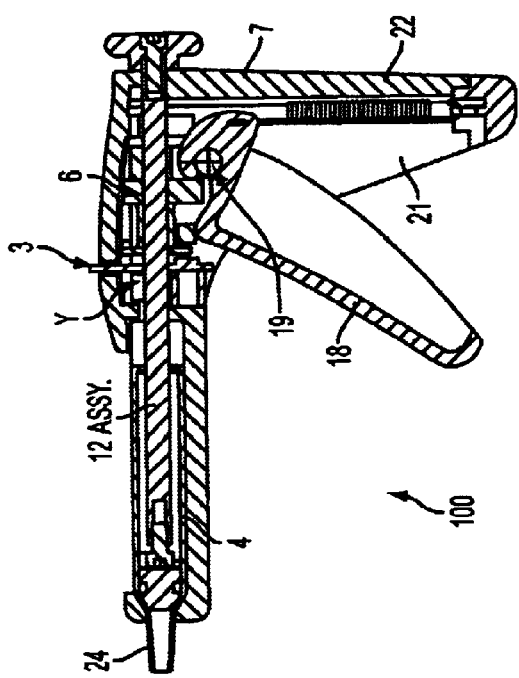
Figure 1D:
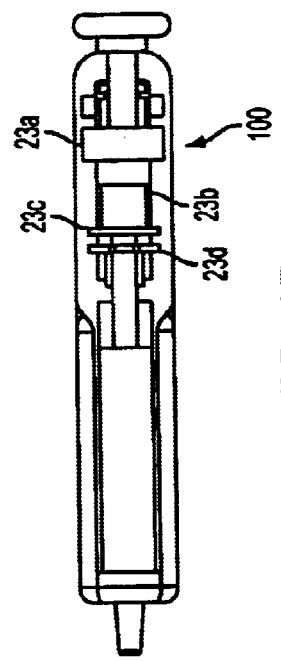
Figure 1A:
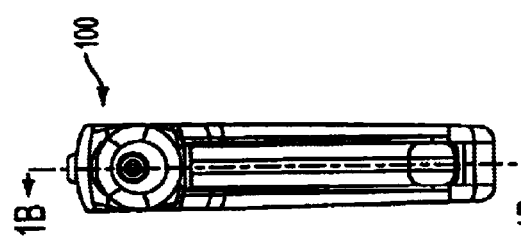
Figure 2:
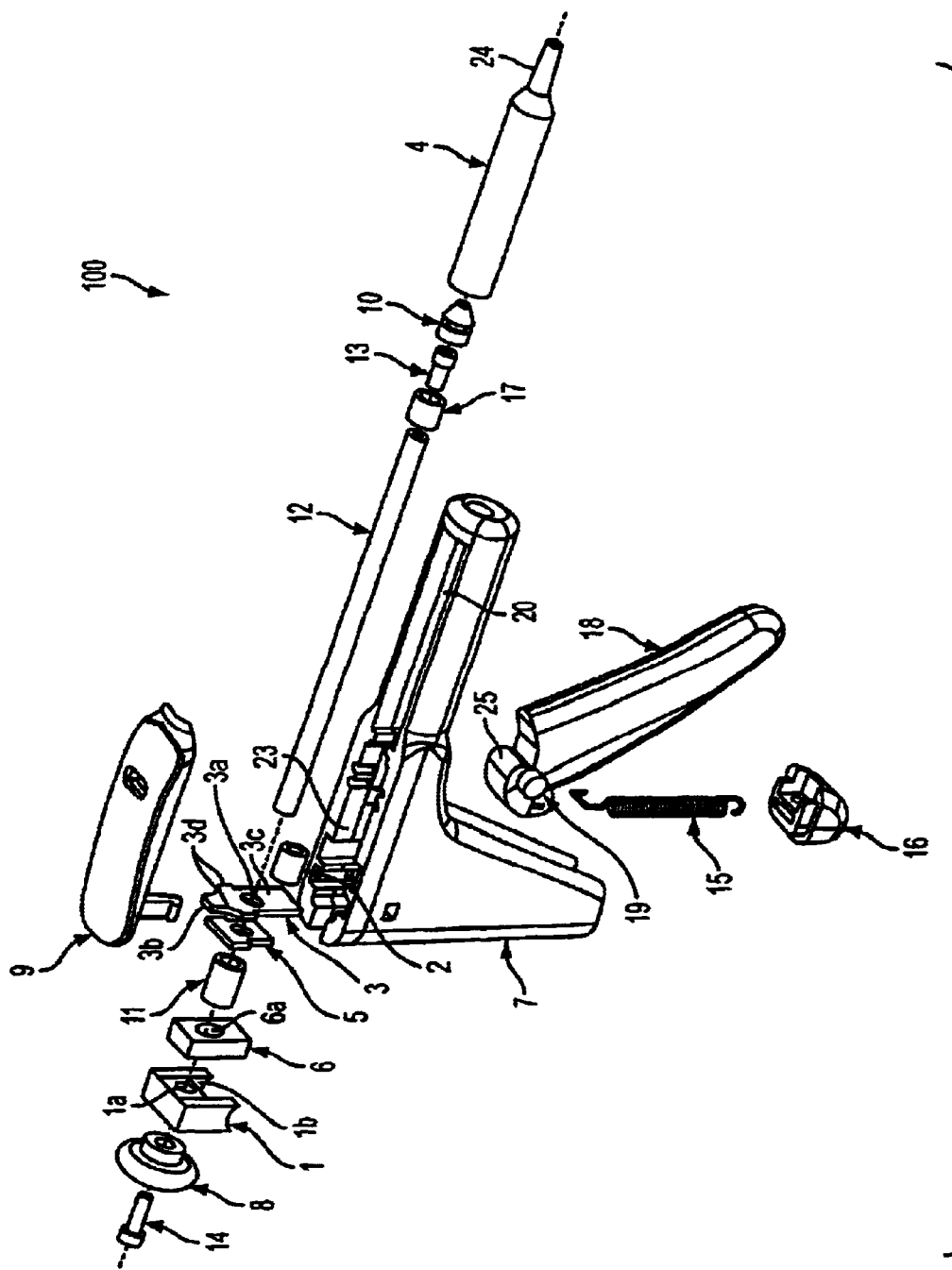
FIG. 2 shows an exploded perspective view of the embodiment of FIGS. 1A–1D.

With reference to FIGS. 1A–1D and 2, a dispenser 100 is disclosed comprising a handle 7 having a forward recess 20 for holding a dental material cartridge 4, and a bottom recess 21 for mounting an actuator 18, rotatable around fulcrum 19 such that an operator is able to squeeze actuator 18 and rear portion 22 of handle 7 in order to rotate actuator 18. Tensile spring 15 is fastened at one end to actuator 18 and at another end to spring holder 16, fixed near a bottom area of rear portion 22, in order for tensile spring 15 to generate a tensile force for returning actuator 18 to a rest position as actuator 18 is released by the operator.

Dispenser 100 further comprises a plunger stop 17 fastened to a forward end of a push rod 12, for example, by screw 13. Push rod 12 and plunger stop 17 extend from a rearward recess 23 of the handle 7, and cart ridge 4 is positioned in forward recess 20 such that longitudinal axes of push rod 12, plunger stop 17 and cartridge 4 are coincident. Piston 10 may be, for example, inserted into an open, rearward end of cartridge 4 so that plunger stop 17 may be driven against piston 10 in order to extrude material through a front nozzle 24 of cartridge 4. Piston 10 provides a seal against an inner circumference of cartridge 4 so that substantially no material is extended at the rearward end of cartridge 4 when piston 10 is driven by plunger stop 17.

Bearing 1 is retained in a rearward cavity 23a of rearward recess 23 and incorporates a bore 1a for receiving push rod 12 with a slip fit. Bearing 1 operates in conjunction with plunger stop 17 to laterally contain push rod 12 so that push rod 12 may be moved along its longitudinal axis. Portions of rear recess 23 may also restrain push rod 12 to travel along its longitudinal axis.

Push rod handle 8 is fastened, for example by means of screw 14, to a rearmost end of push rod 12 extending through rear portion 22 in order to provide a means for the operator to manually adjust the position 10 pushrod 12 (for example, to withdraw push rod 12 to a rearmost position in order to remove and replace cartridge 4).

A driver element 6 is positioned in a second cavity 23b of rear recess 23, adjacent to bearing 1. Driver element 6 comprises a block having a bore 6a with a hole through which the push rod is inserted, the bore 6a having a size slightly larger than that of an outer diameter of the push rod. An upper cam portion 25 of actuator 18 is positioned to come into contact with a lower portion of a rearward surface of driver element 6, such that, when actuator 18 is squeezed by the operator, upper cam portion 25 rotates, engages the rearward surface of driver element 6, and causes driver element 6 to incline so that push rod 12 comes into contact with an edge of the hole in driver element 6. Further rotation of upper cam portion 25 causes driver element 6 to advance, such that a contact resistance (friction) produced at the edge of bore 6a contacting push rod 12 causes push rod 12 to advance together with driver element 6. As push rod 12 advances, plunger stop 17 urges piston 10 forward in cartridge 4 so that composite material is extruded at nozzle 24.

Divider 5 is fixedly mounted in a third cavity 23c in rearward recess 23 adjacent to the second cavity 23b. Divider 5 provides a rear-facing stop surface for receiving driver spring 11. Driver spring 11 contacts a frontward surface of driver element 6 and compresses as driver element 6 advances, thereby generating a force to return driver element 6 to a non-inclined state upon release of actuator 18 by the operator and to return driver element 6 to a position in rearward recess 23 wherein the rearward surface of driver element 6 remains in contact with bearing 1 in its rest position. Bearing 1 includes a slot 1b through which upper cam portion 25 is moved to engage the lower portion of the rearward surface of driver element 6.

A clutch element 3 is located in a fourth cavity 23d in rearward recess 23 adjacent to divider 5. Clutch element 3 comprises a plate having a bore 3a through which push rod 12 is inserted, bore 3a having a size slightly larger than that of the outer diameter of push rod 12. Clutch element 3 is pivotally confined within the fourth cavity 23d by tabs 3d. Lever 3b of clutch element 3 is inserted through a recess 9a of hood 9, which is fixedly snapped into position over rearward recess 23. A lower frontward surface 3c of clutch element 3 is biased by clutch spring 2 so that clutch element 3 remains in a non-inclined position as push rod 12 is advanced by an operator squeezing actuator 18. Once actuator 18 is released, driver spring 11 causes driver element 6 and push rod 12 to move rearward so that driver element 6 and push rod 12 disengage, and with the assistance of clutch spring 2, clutch element 3 inclines, causing push rod 12 to come into contact with an edge of bore 3a. Contact resistance between bore 3a and push rod 12 limits rearward travel of push rod 12 to a distance Y controlled by the geometry of the fourth cavity relative to a compressed length of clutch spring 2 and the position of divider 5.

As push rod 12 moves rearward, clutch element 3 also moves rearward a distance Y defined by the difference between a thickness of slot 23d and a thickness of the portion of clutch element 3 positioned in slot 23d. Biased by clutch spring 2, clutch element 3 also inclines. As a result, a contact resistance between bore 3a and push rod 12 develops from an interference of bore 3a and push rod 12, preventing push rod 12 from retracting further. Piston 10 is able to rearwardly retreat approximately a distance Y in cartridge 4, thereby diminishing the compressive energy in cartridge 4 so that drooling is reduced. It should be noted that clutch spring 2 and drier spring 11 are preferably conventional coil springs selected to provide suitable compressive forces.

Clutch element 3 is located forward of trigger 18 and divider 5 in order to facilitate a compact profile for dispenser 100. Lever 3b can be conveniently pushed by finger pressure to move clutch element 3 to a non-inclined position, and thereby remove contact resistance between clutch element 3 and push rod 12. Push rod 12 may then be retracted, for example, to its most rearward position in order for a spent cartridge 4 to be removed from the dispenser and a new cartridge 4 installed.

The foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A dispenser for dispensing extrudable material from a cartridge, said dispenser comprising:

a housing including first and second recesses, the first recess configured to receive and position the cartridge so that a longitudinal axis of the cartridge is aligned with a longitudinal axis of the first and second recesses;

a plunger movable along the longitudinal axis of the first and second recesses;

a driver element, mounted in the second recess, that selectively engages and moves the plunger in a forward direction along the longitudinal axis of the first and second recesses, and selectively disengages from the plunger to allow the plunger to move in a rearward direction along the longitudinal axis of the first and second recesses; and a clutch element, confined within a cavity in the second recess, that selectively engages the plunger to restrain movement of the plunger in the rearward direction;

such that, when the clutch element engages the plunger, movement of the plunger in the rearward direction is limited to a predetermined distance, said predetermined distance being controlled by a depth of said cavity and a thickness of the clutch element.

2. The dispenser of claim 1, wherein the clutch element disengages from the plunger when the plunger is moved in the forward direction.

3. The dispenser of claim 1, further comprising:
an actuator coupled to the driver element for engaging the driver element to move the plunger in the forward direction.

4. The dispenser of claim 1, wherein the driver element includes:
a bore for receiving the plunger; and
an engagement surface for coupling to the actuator;
such that, when the actuator engages the engagement surface, the driver element is repositioned to cause the bore and plunger to frictionally interfere.

5. The dispenser of claim 1, wherein the clutch element includes:
a bore for receiving the plunger; and
an engagement surface coupled to a clutch spring;
wherein the clutch spring biases the engagement surface to variably position the clutch element according to a directional movement of the plunger, such that the bore and plunger frictionally interfere when the plunger moves in the rearward direction.

6. The dispenser of claim 4, wherein the housing further includes a third recess for mounting a pivot arm of the actuator, the pivot arm being pivotable around a fulcrum and having an upper cam portion for engaging the engagement surface of the driver element.

7. The dispenser of claim 1, wherein the plunger is insertable into a rearward opening of the cartridge such that movement of the plunger in the forward direction causes the extrudable material to be extruded through a front nozzle of the cartridge.

8. The dispenser of claim 7, wherein the plunger includes a plunger stop located at a forward end of the plunger for engaging a piston in the cartridge to extrude extrudable material through the front nozzle of the cartridge.

9. The dispenser of claim 6, further comprising a return spring attached to the pivot arm, the return spring operating to return the pivot arm to a disengaged position when the actuator is released.

10. The dispenser of claim 4, wherein the driver element further includes a driver spring coupled to and biasing the driver element, such that the driver element is repositioned when the actuator is released so that the plunger is movable through the bore.

11. A dispenser for dispensing extrudable material from a cartridge, said dispenser comprising:
a housing including first and second recesses, the first recess configured to receive and position the cartridge so that a longitudinal axis of the cartridge is aligned with a longitudinal axis of the first and second recesses;
a plunger movable along the longitudinal axis of the first and second recesses;
a driver element, mounted in the second recess, that selectively engages and moves the plunger in a forward direction along the longitudinal axis of the first and second recesses, and selectively disengages from the plunger to allow the plunger to move in a rearward direction along the longitudinal axis of the first and second recesses;
a clutch element, mounted in the second recess, that selectively engages the plunger to restrain movement of the plunger in the rearward direction:
a bore for receiving the plunger; and
an engagement surface coupled to a clutch spring;
wherein the clutch spring biases the engagement surface to variably position the clutch element according to a directional movement of the plunger, such that the bore and plunger frictionally interfere when the plunger moves in the rearward direction, and
wherein
wherein the clutch element includes first and second tabs pivotably confined within a cavity in the second recess for variably positioning the clutch elements,
such that, when the clutch element engages the plunger, movement of the plunger in the rearward direction is limited to a predetermined distance.

12. The dispenser of claim 11, wherein the clutch element further includes a lever portion operable to reposition the clutch element so that the plunger is movable through the bore.

13. The dispenser of claim 1, wherein the plunger includes a handle fastened at a rearward end of the plunger extending outwardly from the second recess.

14. A dispenser for dispensing extrudable material, said dispenser comprising:
a cartridge for receiving the extrudable material;
a housing including first recess and second recesses, the first recess configured to receive and position the cartridge so that a longitudinal axis of the cartridge is aligned with a longitudinal axis of the first and second recesses;
a plunger movable along the longitudinal axis of the first and second recesses;
a driver element, mounted in the second recess, that selectively engages and moves the plunger in a forward direction along the longitudinal axis of the first and second recesses, and selectively disengages from the plunger to allow the plunger to move in a rearward direction along the longitudinal axis of the first and second recesses; and
a clutch element, confined within a cavity in the second recess, that selectively engages the plunger to restrain movement of the plunger in the rearward direction;
such that, when the clutch element engages the plunger, movement of the plunger in the rearward direction is limited to a predetermined distance, said predetermined distance being controlled by a depth of said cavity and a thickness of the clutch element.

15. The dispenser of claim 14, wherein the cartridge includes a piston for coupling with a forward end of the plunger, the piston being insertable into a rearward opening of the cartridge to seal an inner circumference of the cartridge while being forwardly urged along the longitudinal axis by the plunger.

16. The dispenser of claim 15, wherein the plunger includes a plunger stop at the forward end of the plunger for coupling with the piston.

17. A dispenser for dispensing dental composite materials from a cartridge, said dispenser comprising:
a housing including first recess and second recesses, the first recess configured to receive and position the cartridge so that a longitudinal axis of the cartridge is aligned with a longitudinal axis of the first and second recesses;

a plunger movable along the longitudinal axis of the first and second recesses;

a driver element, mounted in the second recess, that selectively engages and moves the plunger in a forward direction along the longitudinal axis of the first and second recesses, and selectively disengages from the plunger to allow the plunger to move in a rearward direction along the longitudinal axis of the first and second recesses; and a clutch element, confined within a cavity in the second recess, that selectively engages the plunger to restrain movement of the plunger in the rearward direction;

such that, when the clutch element engages the plunger, movement of the plunger in the rearward direction is limited to a predetermined distance, said predetermined distance being controlled by a depth of said cavity and a thickness of the clutch element.

* * * * *